United States Patent
Koseoglu et al.

(10) Patent No.: US 11,022,588 B2
(45) Date of Patent: Jun. 1, 2021

(54) CHARACTERIZATION OF CRUDE OIL BY SIMULATED DISTILLATION

(71) Applicant: Saudi Arabian Oil Company, Dhahran (SA)

(72) Inventors: Omer Refa Koseoglu, Dhahran (SA); Adnan Al-Hajji, Dhahran (SA); Frederick Marie Adam, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 894 days.

(21) Appl. No.: 15/639,412

(22) Filed: Jun. 30, 2017

(65) Prior Publication Data

US 2017/0363591 A1 Dec. 21, 2017

Related U.S. Application Data

(63) Continuation-in-part of application No. 13/397,312, filed on Feb. 15, 2012, now Pat. No. 9,816,919, and a continuation-in-part of application No. PCT/US2016/012117, filed on Jan. 5, 2016.

(60) Provisional application No. 62/099,690, filed on Jan. 5, 2015, provisional application No. 61/445,183, filed on Feb. 22, 2011.

(51) Int. Cl.
*G01N 30/88* (2006.01)
*G01N 33/28* (2006.01)
*G01N 21/33* (2006.01)

(52) U.S. Cl.
CPC .............. *G01N 30/88* (2013.01); *G01N 21/33* (2013.01); *G01N 33/2823* (2013.01); *G01N 2030/8854* (2013.01); *G01N 2201/129* (2013.01)

(58) Field of Classification Search
CPC .............. G01N 30/88; G01N 33/2823; G01N 2030/8854
See application file for complete search history.

(56) References Cited

U.S. PATENT DOCUMENTS

| | | | |
|---|---|---|---|
| 3,617,501 A | 11/1971 | Eng | |
| 3,896,312 A | 7/1975 | Brown | |
| 4,251,870 A | 2/1981 | Jaffe | |
| 4,897,177 A | 1/1990 | Nadler | |
| 4,971,915 A | 11/1990 | Schwartz et al. | |

(Continued)

FOREIGN PATENT DOCUMENTS

| | | |
|---|---|---|
| CA | 2781273 A1 | 12/2013 |
| EP | 0305090 A2 | 8/1988 |

(Continued)

OTHER PUBLICATIONS

Boduszynski, M. M., & Altgelt, K. H. (1992). Composition of heavy petroleums. 4. Significance of the extended atmospheric equivalent boiling point (AEBP) scale. Energy & fuels, 6(1), 72-76. (Year: 1992).*

(Continued)

*Primary Examiner* — Bijan Mapar
(74) *Attorney, Agent, or Firm* — Abelman, Frayne and Schwab

(57) ABSTRACT

A system and a method is provided for calculating and assigning one or more indicative properties (e.g., cetane number, pour point, cloud point and/or aniline point) of a fractions of a crude oil sample based upon gas chromatographic simulated distillation data.

22 Claims, 3 Drawing Sheets

(56) References Cited

U.S. PATENT DOCUMENTS

| | | | |
|---|---|---|---|
| 4,988,446 | A | 1/1991 | Haberman |
| 5,121,337 | A | 6/1992 | Brown |
| 5,223,714 | A | 6/1993 | Maggard |
| 5,266,800 | A | 11/1993 | Mullins |
| 5,304,807 | A | 4/1994 | Lin |
| 5,424,959 | A | 6/1995 | Reyes |
| 5,452,232 | A | 9/1995 | Espinosa et al. |
| 5,475,612 | A | 12/1995 | Espinosa |
| 5,490,085 | A | 2/1996 | Lambert et al. |
| 5,572,030 | A | 11/1996 | Ranson et al. |
| 5,600,134 | A | 2/1997 | Ashe et al. |
| 5,602,755 | A | 2/1997 | Ashe et al. |
| 5,656,810 | A | 8/1997 | Alfano et al. |
| 5,699,269 | A | 12/1997 | Ashe et al. |
| 5,699,270 | A | 12/1997 | Ashe et al. |
| 6,070,128 | A | 5/2000 | Descales |
| 6,258,987 | B1 | 7/2001 | Schmidt et al. |
| 6,275,775 | B1 | 8/2001 | Baco |
| 6,490,029 | B1 | 12/2002 | Cho |
| 6,602,403 | B1 | 8/2003 | Steffens et al. |
| 6,611,735 | B1 | 8/2003 | Henly |
| 6,633,043 | B2 | 10/2003 | Hegazi |
| 6,662,116 | B2 | 12/2003 | Brown |
| 6,711,532 | B1 | 3/2004 | Spieksma |
| 6,841,779 | B1 | 1/2005 | Roehner et al. |
| 6,893,874 | B2 | 5/2005 | Stark |
| 7,126,332 | B2 | 10/2006 | Blanz |
| 7,173,239 | B2 | 2/2007 | DiFoggio |
| 7,560,711 | B2 | 7/2009 | Hegazi |
| 7,598,487 | B2 | 10/2009 | Qian |
| 8,714,246 | B2 | 5/2014 | Pop et al. |
| 8,930,149 | B1 | 1/2015 | Koseoglu et al. |
| 9,285,307 | B2 | 3/2016 | Koseoglu et al. |
| 9,423,391 | B2 | 8/2016 | Koseoglu et al. |
| 9,429,556 | B2 | 8/2016 | Koseoglu et al. |
| 9,778,240 | B2 | 10/2017 | Koseoglu et al. |
| 9,816,919 | B2 | 11/2017 | Koseoglu et al. |
| 2002/0052769 | A1 | 5/2002 | Navani et al. |
| 2003/0141459 | A1 | 7/2003 | Hegazi et al. |
| 2003/0195708 | A1 | 10/2003 | Brown |
| 2005/0091020 | A1* | 4/2005 | Cheng .................... G05B 17/02 703/12 |
| 2005/0109934 | A1 | 5/2005 | David |
| 2005/0173298 | A1 | 8/2005 | Wellington |
| 2006/0043004 | A1 | 3/2006 | Rose |
| 2006/0047444 | A1 | 3/2006 | Brown |
| 2006/0069295 | A1* | 3/2006 | Dieckmann .............. C07C 7/20 585/3 |
| 2006/0142955 | A1 | 6/2006 | Jones |
| 2007/0050154 | A1 | 3/2007 | Albahri |
| 2007/0114377 | A1* | 5/2007 | Qian ...................... B01D 59/44 250/282 |
| 2007/0231912 | A1 | 10/2007 | Reischman et al. |
| 2007/0295640 | A1 | 12/2007 | Tan et al. |
| 2008/0037006 | A1 | 2/2008 | Canas Triana |
| 2008/0040051 | A1 | 2/2008 | Franklin et al. |
| 2008/0206887 | A1 | 8/2008 | Chen |
| 2008/0248967 | A1 | 10/2008 | Butler et al. |
| 2008/0253426 | A1* | 10/2008 | Voelkening ............. G01N 25/02 374/27 |
| 2008/0260584 | A1 | 10/2008 | Gudde et al. |
| 2009/0011517 | A1 | 1/2009 | Hodges |
| 2009/0180949 | A1 | 7/2009 | Cui |
| 2009/0279072 | A1 | 11/2009 | Arakawa |
| 2009/0290144 | A1 | 11/2009 | Hegazi |
| 2009/0316139 | A1 | 12/2009 | Shrestha |
| 2010/0049681 | A1 | 2/2010 | Pradhan |
| 2010/0113311 | A1 | 5/2010 | Eccleston et al. |
| 2010/0204925 | A1 | 8/2010 | Albahri |
| 2010/0211329 | A1 | 8/2010 | Farquharson et al. |
| 2010/0218585 | A1 | 9/2010 | Chawla |
| 2011/0152136 | A1 | 6/2011 | Hughes et al. |
| 2011/0308996 | A1 | 12/2011 | Choudhary |
| 2012/0171151 | A1 | 7/2012 | Thomassian |
| 2014/0075827 | A1 | 3/2014 | Gonzalez et al. |
| 2014/0156241 | A1 | 6/2014 | Kumar et al. |
| 2015/0106027 | A1 | 4/2015 | Koseoglu et al. |
| 2015/0106028 | A1 | 4/2015 | Koseoglu et al. |
| 2015/0106029 | A1 | 4/2015 | Koseoglu et al. |
| 2015/0106031 | A1 | 4/2015 | Koseoglu et al. |
| 2015/0112610 | A1 | 4/2015 | Koseoglu |
| 2015/0112611 | A1 | 4/2015 | Koseoglu |
| 2016/0011102 | A1 | 1/2016 | Koseoglu et al. |
| 2016/0187253 | A1 | 6/2016 | Koseoglu et al. |
| 2016/0195481 | A1 | 7/2016 | Koseoglu |
| 2016/0195507 | A1 | 7/2016 | Koseoglu |
| 2016/0195508 | A1 | 7/2016 | Ai-Hajji |
| 2016/0377589 | A1 | 12/2016 | Koseoglu |
| 2017/0003217 | A1 | 1/2017 | Koseoglu |
| 2017/0363540 | A1 | 12/2017 | Koseoglu |
| 2017/0363591 | A1 | 12/2017 | Koseoglu |
| 2017/0363602 | A1 | 12/2017 | Koseoglu |
| 2017/0363603 | A1 | 12/2017 | Koseoglu |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

ASTM, Designation: D976-91(2000)e1 (Historical Version), published Apr. 2000. (Year: 2000).*

Adhvaryu, A. et al., Quantitative NMR Spectroscopy for the Prediction of Base Oil Properties, Tribology Transactions, vol. 43, No. 2, 2000, pp. 245-250.

Albahri, T. et al, Octane Number and Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

Bowden, J. et al., Octane-Cetane Relationship, 1974, NTIS, p. 8.

Chemstations, Inc, Physical Properties User's Guide, 2004, Chemstations Inc., Ver. 5.4, pp. 18-22.

Cookson, D.J. et al., Investigation of the Chemical Basis of Diesel Fuel Properties, Energy & Fuels, vol. 2, No. 6, 1988, pp. 854-860.

Duvekot, C., Fast Analysis of Paraffins, iso-Paraffins, Olefins, iso-Olefins, Naphthenes and Aromatics in Hydrocarbon Streams, Varian, Inc, 2008, pp. 1-4.

Evokimov, I, et al, Potential of UV-Visible Absorption Spectroscopy for characterizing Crude Petroleum Oils, Oil an Gas Business, 2007, 21 pages.

Falla, F, et al., Characterization of crude petroleum by NIR, Journal of Petroleum Science and Engineering, vol. 51, 2006, pp. 127-137.

Fernandez-Lima, F. et al., Petroleum Crude Oil Characterization by IMS-MS and FTICR MS, 2009, American Chemical Society, Ed. 81, pp. 9941-9945.

Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.

(56) References Cited

OTHER PUBLICATIONS

Hasan, M.U. et al., Structural characterization of Saudi Arabian heavy crude oil by n.m.r. spectroscopy, Fuel, vol. 62, 1983, pp. 518-523.

Hidajat, K, et al., Quality characterisation of crude oils by partial least square calibration of NIR spectral profiles, Near Infrared Spectrosc, vol. 8, pp. 53-59, 2000.

Jokuty, P. et al., Hydrocarbon Groups and Their Relationships to Oil Properties and Behavior, 1995, Published by Whiticar Scientific, p. 11.

Khanmohammadi, M, et al., Characterization of petroleum-based products by infrared spectroscopyu and chemometrics, Trac Trends in Analytical Chem, vol. 35, 2012.

Kok, M, et al., High pressure TGA analysis of crude oils, Thermochimica Acta., vol. 287, No. 1, 1996, pp. 91-99.

Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.

Pande, S., et al., Cetana Number Predictions of a Trial Index Based on Compositional Analysis, American Chemical Society, 1989, pp. 308-312.

Patra, D, et al, Determination of Synchronous Fluorescence Scan Parameters for Certain Petroleum Products, Journal of Scientific & Industrial Research, Apr. 1, 2000, pp. 300-305.

Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).

Pereira, Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.

Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.

Shea, T.M., Modeling Base Oil Properties using NMR Spectroscopy and Neural Networks, Tribology Transactions, vol. 46, No. 3, 2003, pp. 296-302.

Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.

Speight, Handbook of Petroleum Product Analysis, 2002.

Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.

University of Oldenburg, Institute of Physics, Catalogue of Optical Spectra of Oils, Jan. 2005, retrieved from http://as.physik.uni-oldenburg.de/data/spectra/indez.htm, 6 pages.

Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.

PCT/US2016/012117, International Search Report and Written Opinion dated Jun. 9, 2016, 14 pages.

\* cited by examiner

CHARACTERIZATION OF CRUDE OIL BY SIMULATED DISTILLATION

RELATED APPLICATIONS

This application is a Continuation-in-Part of U.S. patent application Ser. No. 13/397,312 filed Feb. 15, 2012, claiming priority from U.S. Provisional Patent Application No. 61/445,183 filed Feb. 22, 2011; and PCT/US2016/012117 filed Jan. 5, 2016, claiming priority from U.S. Provisional Patent Application No. 62/099,690 filed Jan. 5, 2015, the disclosures of which are hereby incorporated by reference in their entireties.

FIELD OF THE INVENTION

This invention relates to a method and process for the evaluation of samples of crude oil and its fractions by simulated distillation (SD).

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and others elements in quantities that impact the refinery processing of the crude oil fractions. Light crude oils or condensates can contain sulfur in concentrations as low as 0.01 W % of sulfur; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two phases separate is recorded as the aniline point or mixed aniline point.

To determine these properties of gas oil or naphtha fractions conventionally, these fractions have to be distilled off from the crude oil and then measured/determined using various analytical methods that are laborious, costly and time consuming.

New rapid and direct methods to help better understand crude oil compositions and properties from analysis of whole crude oil will save producers, marketers, refiners and/or other crude oil users substantial expense, effort and time. Therefore, a need exists for an improved system and method for determining indicative properties of crude fractions from different sources.

SUMMARY OF THE INVENTION

Systems and methods for determining one or more indicative properties of a hydrocarbon sample are provided. Indicative properties (e.g., cetane number, pour point, cloud point and aniline point) of a gas oil fraction in crude oil samples are assigned as a function of the density and simulated distillation data for a crude oil sample. The correlations also provide information about the gas oil indicative properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings, in which.

DETAILED DESCRIPTION OF INVENTION

Figure 1:
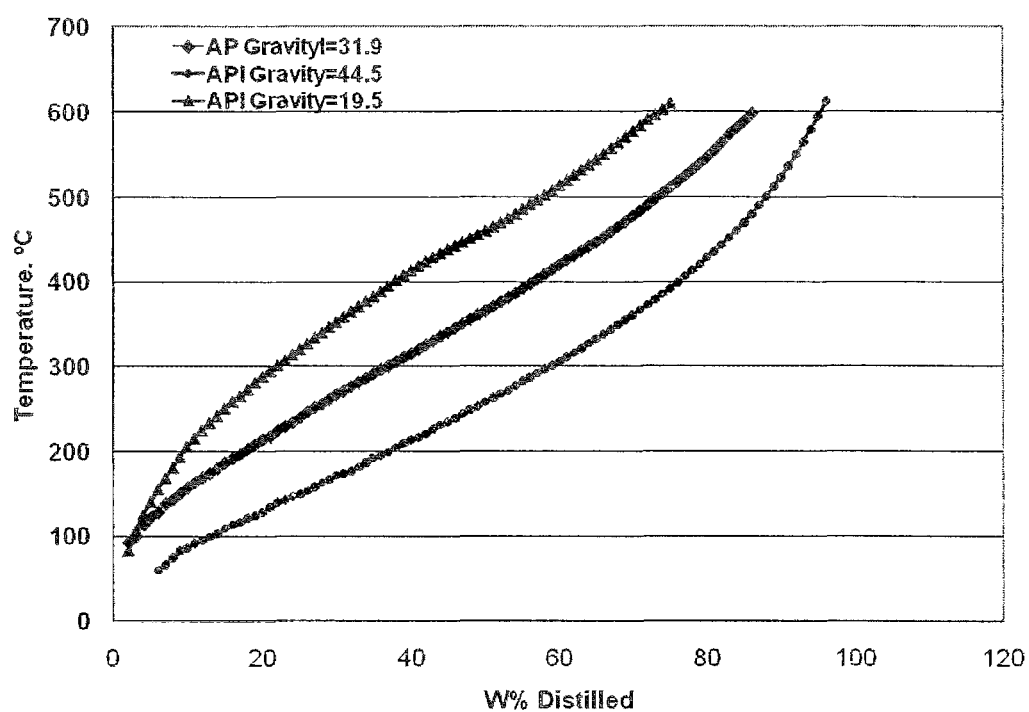
FIG. 1 is a graphic plot of simulated distillation data obtained from gas chromatography for three types of crude oil.

A system and method is provided for determining one or more indicative properties of a hydrocarbon sample. Indicative properties (e.g., cetane number, pour point, cloud point and aniline point) of a gas oil fraction in crude oil samples are assigned as a function of the density and data obtained from simulated distillation data of a crude oil sample. The correlations also provide information about gas oil indicative properties without fractionation/distillation (crude oil assays) and will help producers, refiners, and marketers to benchmark the oil quality and, as a result, valuate the oils without performing the customary extensive and time-consuming crude oil assays. The currently used crude oil assay method is costly in terms of money and time. It costs about $50,000 US and takes two months to complete one assay. With the method and system herein, the crude oil can be classified as a function of SD data, and thus decisions can be made for purchasing and/or processing.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

In the system and method herein, crude oil simulated distillation data is obtained by a suitable known or to be developed simulated distillation processes. Simulated distillation (SD) is a technique which separates individual hydrocarbon components in the order of their boiling points, and is used to simulate laboratory-scale physical distillation procedures. The separation can be accomplished with a gas chromatograph equipped with a chromatography column coated with a nonpolar (hydrocarbon-like) stationary phase, an oven and injector which can be temperature programmed. A flame ionization detector (FID) is used for detection and measurement of the hydrocarbon analytes. The SD analysis result provides a quantitative percent mass yield as a function of boiling point of the hydrocarbon components of the sample being analyzed. The chromatographic elution times of the hydrocarbon components are calibrated to the atmospheric equivalent boiling point (AEBP) of the individual n-alkane as described in a method from the ASTM by using n-alkane (n-paraffin) reference material. In the SD method ASTM D2887, the n-alkane calibration reference covers the boiling range 55-538° C. (100-1000° F.) which covers the n-alkanes with a chain length of about C5-C44.

Alternative methods may be used, including ASTM D5236, ASTM D86, ASTM D5399, ASTM D6352-04, ASTM D7213-05e1, ASTM D7398-07, ASTM D7169-05, ASTM D7096-10, ASTM D7500-10, ASTM D5307-97, ASTM D1160, ASTM D2892, or any other methods based upon gas chromatography, true boiling point distillation, supercritical fluid chromatography, and equilibrium flash. There are well-known correlations to convert distillation numbers: for example, if the true boiling point distillation (ASTM D2892) is known, the SD data (ASTM D2887) can be estimated. While there are not yet ASTM methods using supercritical fluid chromatography, non-standardized lab methods are known.

In the high temperature simulated distillation method (HTSD), the n-alkane calibration reference (a hydrogenated polyolefin wax, polywax 655) covers the boiling range 36-750° C. (97-1382° F.) which covers the n-alkanes with a chain length of about C5-C120. A key difference between ASTM D2887 and HTSD is the ability of HTSD to handle residue-containing samples (i.e. material boiling >538° C. or 1000° F.).

SD and laboratory-scale physical distillation methods are routinely used for determining boiling ranges of petroleum crude oils and refined products. The boiling points with yield profile data of these materials are used by refinery engineers to make operational decisions to improve product yields and product quality. SD is valuable for, and can improve results from, computer modeling of refining processes for improvements in design and process optimization. Precise yield correlations between HTSD and crude assay distillation (a procedure which uses methods ASTM D5236 and D2892) have allowed HTSD to be successfully used in place of the physical distillation procedures. A typical simulated distillation chart obtained from a gas chromatogram of crude oil is shown in FIG. 1, where the W % of distilled fractions is plotted against the boiling temperature.

The indicative properties (e.g., the cetane number, pour point, cloud point and aniline point) of the gas oil fraction, e.g., boiling in the range of 150-400° C. and in certain embodiments in the range of 180-370° C., can be assigned as a function of the density and the mid boiling point or weighted average boiling point of the gas oil or whole crude oil ($T_{MBP}$), measured in Kelvin.

Figure 2:
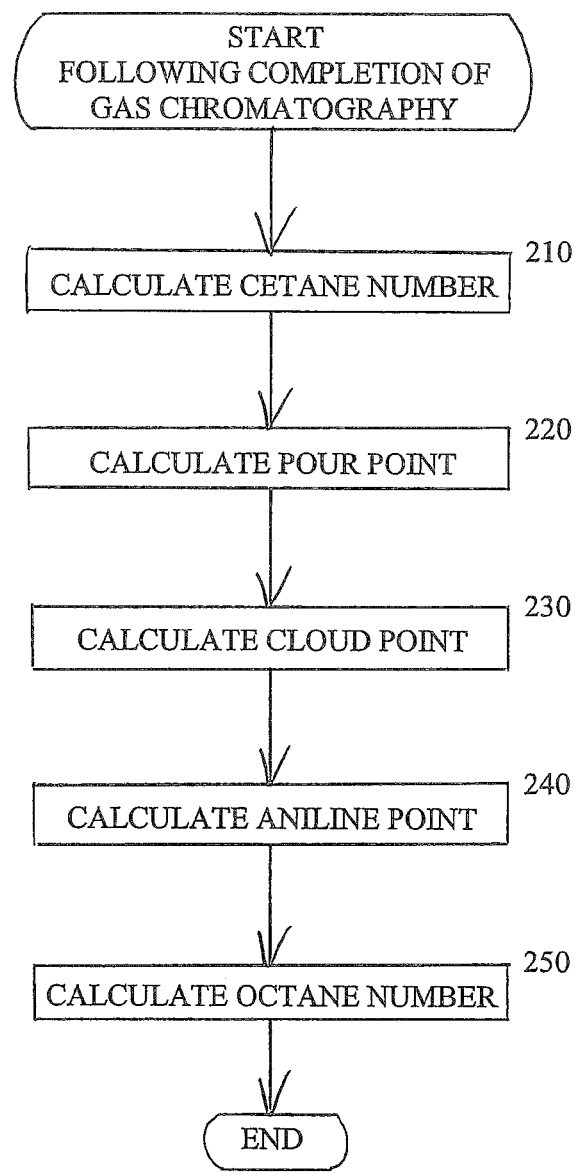
FIG. 2 is a process flow diagram of steps carried out to establish a value for indicative properties of a gas oil fraction, using the system and method herein.

FIG. 2 shows a process flowchart of steps in a method according to one embodiment herein that occur after gas chromatography is completed and the results are tabulated. In step 210, the cetane number is calculated. In step 220, the pour point is calculated. In step 230, the cloud point is calculated. In step 240, the aniline point is calculated. In step 250, the octane number is calculated. While FIG. 2 shows the steps performed sequentially, they can be performed in parallel or in any order. In certain embodiments, only one or more or steps 210, 220, 230, 240, 250 are carried out. That is, $$\text{Indicative Property} = f(\text{density}_{crude\ oil}, T_{MBP\ gas\ oil}) \quad (1a);$$

$$\text{Indicative Property} = f(\text{density}_{crude\ oil}, T_{MBP\ crude\ oil}) \quad (1b);$$

Equations (2) through (5) show that the cetane number, pour point, cloud point and aniline point can be assigned as a function of the density and simulated distillation of crude oils.

$$\text{Cetane Number } (CET) = K_{CET} + X1_{CET}*DEN + X2_{CET}*DEN^2 + X3_{CET}*DEN^3 + X4_{CET}*(T_{MBP}/1000) + X5_{CET}*(T_{MBP}/1000)^2 + X6_{CET}*(T_{MBP}/1000)^3 + X7_{CET}*DEN*(T_{MBP}/1000) \quad (2);$$

$$\text{Pour Point } (PP) = K_{PP} + X1_{PP}*DEN + X2_{PP}*DEN^2 + X3_{PP}*DEN^3 + X4_{PP}*(T_{MBP}/1000) + X5_{PP}*(T_{MBP}/1000)^2 + X6_{PP}*(T_{MBP}/1000)^3 + X7_{PP}*DEN*(T_{MBP}/1000) \quad (3);$$

$$\text{Cloud Point } (CP) = K_{CP} + X1_{CP}*DEN + X2_{CP}*DEN^2 + X3_{CP}*DEN^3 + X4_{CP}*(T_{MBP}/1000) + X5_{CP}*(T_{MBP}/1000)^2 + X6_{CP}*(T_{MBP}/1000)^3 + X7_{CP}*DEN*(T_{MBP}/1000) \quad (4);$$

$$\text{Aniline Point } (AP) = K_{AP} + X1_{AP}*DEN + X2_{AP}*DEN^2 + X3_{AP}*DEN^3 + X4_{AP}*(T_{MBP}/1000) + X5_{AP}*(T_{MBP}/1000)^2 + X6_{AP}*(T_{MBP}/1000)^3 + X7_{AP}*DEN*(T_{MBP}/1000) \quad (5);$$

where:
DEN=density of the crude oil sample;
$T_{MBP}$=mid boiling point of the gas oil or crude oil (derived from the simulated distillation curves of crude oils);
and $K_{CET}$, $X1_{CET}$-$X7_{CET}$, $K_{PP}$, $X1_{CP}$-$X7_{CP}$, $K_{CP}$, $X1_{CP}$-$X7_{CP}$, $K_{AP}$, and $X1_{AP}$-$X7_{AP}$ are constants.

As an alternative to the mid boiling point a weighted average boiling point (WABP) can be used, shown in equation (6), below.

$$WABP = \frac{(T_{10}*10) + (T_{30}*30) + (T_{50}*50) + (T_{70}*70) + (T_{90}*90)}{10+30+50+70+90}, \quad (6)$$

where $T_{10}$ is the boiling temperature of oil determined when 10 W % or V % of the fraction is recovered during the distillation, and where $T_{30}$, $T_{50}$, $T_{70}$ and $T_{90}$ are determined accordingly.

Figure 3:
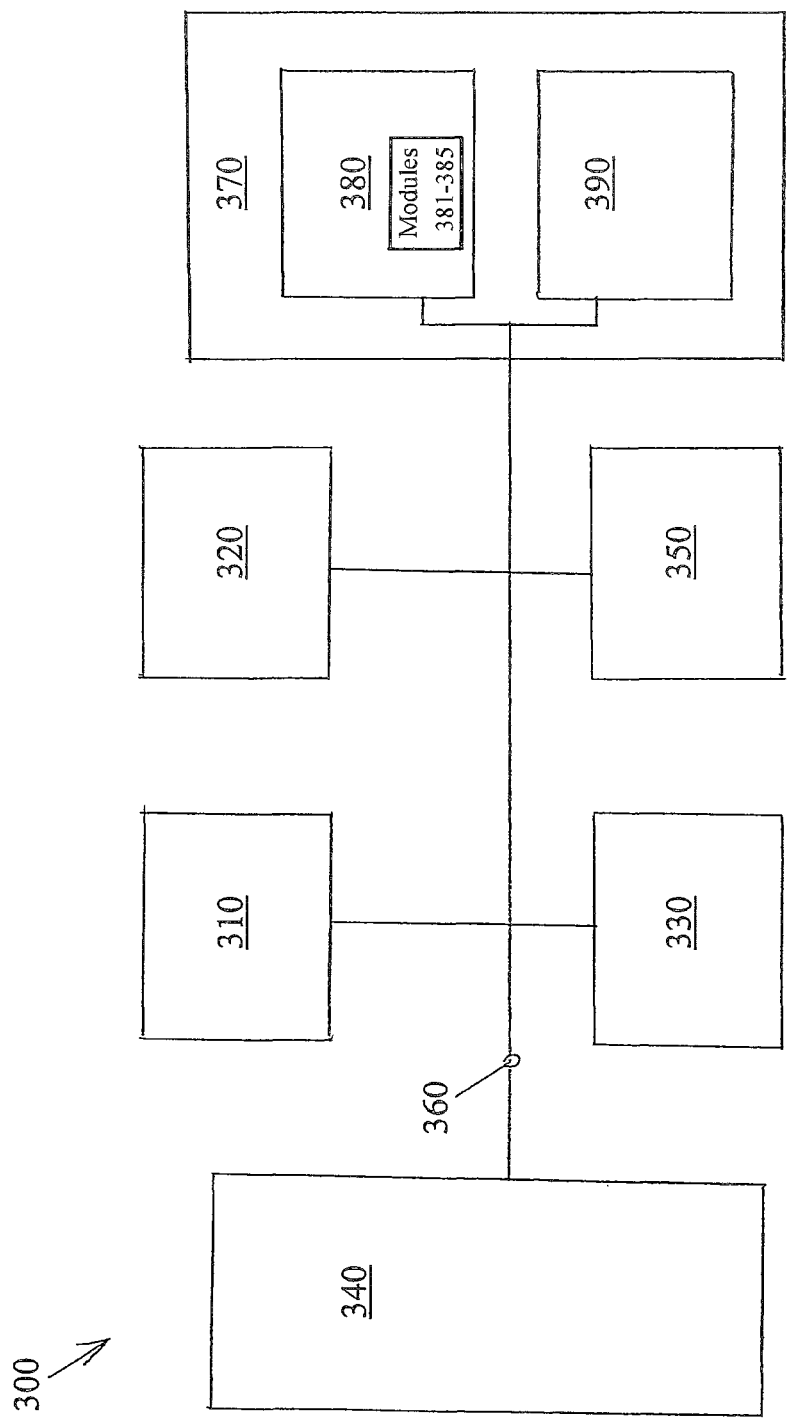
FIG. 3 is a block diagram of a component of a system for implementing the invention, according to one embodiment.

An exemplary block diagram of a computer system 300 by which indicative property calculation modules can be implemented is shown in FIG. 3. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, and in particular stores one or more indicative property calculation modules 381-385 such as cetane number calculation module 381, a pour point calculation module 382, a cloud point calculation module 383, an aniline point calculation module 384, and an octane number calculation module 385. Data storage memory 390 stores data used and/or generated by the one or more modules of the present system, including density of the crude oil sample, SD data or portions thereof used by the one or more modules of the present system, and calculated indicative properties generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

Example 1

A set of constants $K_{CET}$, $X1_{CET}$-$X7_{CET}$, $K_{PP}$, $X1_{PP}$-$X7_{PP}$, $K_{CP}$, $X1_{CP}$-$X7_{CP}$, $K_{AP}$, and $X1_{AP}$-$X7_{AP}$ was determined using linear regression. These constants are given in Table 3.

TABLE 3

| Property | Cetane Number (CET) | Pour Point (PP) | Cloud Point (CP) | Aniline Point (AP) |
|---|---|---|---|---|
| K | 544509.8 | 1344488.4 | 395024.0 | 24390.7 |
| X1 | −1932359.8 | −4907366.2 | −1429569.6 | −49357.1 |
| X2 | 2161099.3 | 5503008.0 | 1604628.0 | 52455.3 |
| X3 | −796440.7 | −2031119.7 | −592968.1 | −18616.3 |
| X4 | 142762.7 | 527938.4 | 136360.5 | −41985.4 |
| X5 | −177339.2 | −699945.0 | −177392.5 | 65171.0 |
| X6 | 90209.8 | 361176.8 | 91570.3 | −33881.4 |
| X7 | −30458.6 | −87436.2 | −25137.2 | 408.8 |

Example 2

The following example is provided to demonstrate an application of equations (2) through (5). A sample of Arabian medium crude with a 15° C./4° C. density of 0.8828 Kg/l (e.g., at 15° C./4° C. using the method described in ASTM D4052) was analyzed by gas chromatography using the ASTM D2887 method. The simulated distillation data is shown in Table 4:

TABLE 4

| W % | Temp. ° C. |
|---|---|
| 0 | |
| 1 | |
| 2 | 37 |
| 3 | 68 |
| 4 | 83 |
| 5 | 94 |
| 6 | 100 |
| 7 | 113 |
| 8 | 121 |
| 9 | 127 |
| 10 | 138 |
| 11 | 144 |
| 12 | 151 |
| 13 | 157 |
| 14 | 165 |
| 15 | 172 |
| 16 | 175 |
| 17 | 185 |
| 18 | 191 |
| 19 | 196 |
| 20 | 204 |
| 21 | 210 |
| 22 | 216 |
| 23 | 222 |
| 24 | 229 |
| 25 | 235 |
| 26 | 241 |
| 27 | 249 |
| 28 | 255 |
| 29 | 261 |
| 30 | 267 |
| 31 | 272 |
| 32 | 279 |
| 33 | 285 |
| 34 | 290 |
| 35 | 297 |
| 36 | 303 |
| 37 | 308 |
| 38 | 315 |
| 39 | 319 |
| 40 | 326 |
| 41 | 331 |
| 42 | 337 |
| 43 | 342 |
| 44 | 348 |
| 45 | 354 |
| 46 | 360 |
| 47 | 366 |
| 48 | 372 |
| 49 | 378 |
| 50 | 384 |
| 51 | 390 |
| 52 | 396 |
| 53 | 402 |
| 54 | 409 |
| 55 | 415 |
| 56 | 422 |
| 57 | 428 |
| 58 | 434 |
| 59 | 440 |
| 60 | 446 |
| 61 | 452 |
| 62 | 458 |
| 63 | 465 |
| 64 | 471 |
| 65 | 478 |

TABLE 4-continued

| W % | Temp. ° C. |
|---|---|
| 66 | 485 |
| 67 | 492 |
| 68 | 499 |
| 69 | 506 |
| 70 | 513 |
| 71 | 520 |
| 72 | 528 |
| 73 | 535 |
| 74 | 543 |
| 75 | 551 |
| 76 | 559 |
| 77 | 567 |
| 78 | 575 |
| 79 | 583 |
| 80 | 592 |
| 81 | 599 |
| 82 | 608 |

The mid boiling point of the crude oil is taken from the data at the 50 W % point, which is 384° C. (657 K). The calculations below are shown with temperature expressed in Kelvin, and using a density at 15° C./4° C. using the method described in ASTM D4052.

Applying equation 2 and the constants from Table 3, $$\text{Cetane Number } (CET) =$$
$$K_{CET} + X1_{CET} * DEN + X2_{CET} * DEN^2 + X3_{CET} * DEN^3 +$$
$$X4_{CET} * (T_{MBP}/1000) + X5_{CET} * (T_{MBP}/1000)^2 +$$
$$X6_{CET} * T(T_{MBP}/1000)^3 + X7_{CET} * DEN * (T_{MBP}/1000) =$$
$$(544509.8) + (-1932359.8)(0.8828) + (2161099.3)(0.8828)^2 +$$
$$(-796440.7)(0.8828)^3 + (142762.7)(657/1000) +$$
$$(-177339.2)(657/1000)^2 + (90209.8)(657/1000)^3 +$$
$$(-30458.6)(0.8828)(657/1000) = 59$$

Applying equation 3 and the constants from Table 3, $$\text{Pour Point } (PP) = K_{PP} + X1_{PP} * DEN + X2_{PP} * DEN^2 +$$
$$X3_{PP} * DEN^3 + X4_{PP} * (T_{MBP}/1000) + X5_{PP} * (T_{MBP}/1000)^2 +$$
$$X6_{PP} * (T_{MBP}/1000)^3 + X7_{PP} * DEN * (T_{MBP}/1000) =$$
$$(1344488.4) + (-4907366.2)(0.8828) + (5503008.06)(0.8828)^2 +$$
$$(-2031119.7)(0.8828)^3 + (527938.4)(657/1000) +$$
$$(-699945.0)(657/1000)^2 + (361176.8)(654/1000)^3 +$$
$$(-87436.2)(0.8828)(657/1000) = -10$$

Applying equation 4 and the constants from Table 3, $$\text{Cloud Point } (CP) = K_{CP} + X1_{CP} * DEN + X2_{CP} * DEN^2 +$$
$$X3_{CP} * DEN^3 + X4_{CP} * (T_{MBP}/1000) + X5_{CP} * (T_{MBP}/1000)^2 +$$
$$X6_{CP} * (T_{MBP}/1000)^3 + X7_{CP} * DEN * (T_{MBP}/1000) =$$
$$(395024.0) + (-1429569.6)(0.8828) + (1604628.0)(0.8828)^2 +$$
$$(-592968.1)(0.8828)^3 + (136360.5)(657/1000) +$$
$$(-177392.5)(657/1000)^2 + (91570.3)(657/1000)^3 +$$
$$(-25137.2)(0.8828)(657/1000) = -10$$

Applying equation 5 and the constants from Table 3, $$\text{Aniline Point } (AP) =$$
$$K_{AP} + X1_{AP} * DEN + X2_{AP} * DEN^2 + X3_{AP} * DEN^3 +$$
$$X4_{AP} * (T_{MBP}/1000) + X5_{AP} * (T_{MBP}/1000)^2 +$$
$$X6_{AP} * (T_{MBP}/1000)^3 + X7_{AP} * DEN * (T_{MBP}/1000) =$$
$$(24390.7) + (-49357.1)(0.8828) + (52455.3)(0.8828)^2 + (-18616.3)$$
$$(0.8828)^3 + (-41985.4)(657/1000) + (65171.0)(657/1000)^2 +$$
$$(-33881.4)(657/1000)^3 + (408.8)(0.8828)(657/1000) = 66.$$

Accordingly, as shown in the above example, indicative properties including cetane number, pour point, cloud point and aniline point can be assigned to the crude oil samples without fractionation/distillation (crude oil assays).

Example 3

An example calculation of WABP is presented below. When the sample is distilled, the boiling point of the sample is determined to be 149° C. when 10 W % of the sample is recovered, 230° C. when 30 W % of the sample is recovered, 282° C. when 50 W % of the sample is recovered, 325° C. when 70 W % of the sample is recovered, and 371° C. when 90 W % of the sample is recovered. Thus, $T_{10}$ is 149° C., and the other values are similarly determined.

$$WABT = \frac{[149*10 + 230*30 + 282*50 + 325*70 + 371*90]}{[10 + 30 + 50 + 70 + 90]}$$
$$= 315$$

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figures; however, modifications will be apparent to those of ordinary skill in the art and the scope of protection for the invention is to be defined by the claims that follow.

We claim:

1. A system for assigning an indicative property to a fraction of an oil sample, the oil sample selected from the group consisting of crude oils, bitumens, shale oils, and heavy oils from refinery process units including hydrotreating, hydroprocessing, fluid catalytic cracking, coking, visbreaking or coal liquefaction, the system comprising:
   a gas chromatograph that outputs simulated distillation (SD) data;
   a non-volatile memory device that stores calculation modules and data, the data including the SD data indicative of weight percent amount distilled across a range of boiling points of the oil sample;
   a processor coupled to the non-volatile memory device; and
   a calculation module that calculates and assigns the indicative property of a fraction of the oil sample as a function of a mid-boiling point of the oil sample determined from the SD data or an average boiling point of the oil sample determined from the SD data, and a density of the oil sample, and that stores the indicative property into the non-volatile memory device,
   wherein the function is two-variable polynomial equation, wherein the two variables are the mid-boiling point of the oil sample determined from the SD data or the average boiling point of the oil sample determined from the SD data, and the density of the oil sample, and
   wherein the indicative property is used to determine one or more of engine/fuel performance, usability, flow characteristic, or composition of the gas oil fraction or the naphtha fraction of the oil sample.

2. A method for assigning an indicative property to a fraction of an oil sample, the oil sample selected from the group consisting of crude oils, bitumens, shale oils, and heavy oils from refinery process units including hydrotreating, hydroprocessing, fluid catalytic cracking, coking, visbreaking or coal liquefaction, the method comprising:
   operating a gas chromatograph to output simulated distillation (SD) data;
   receiving, by a non-volatile memory of a computer, the outputted SD data indicative of weight percent amount distilled across a range of boiling points of the oil sample;
   using a processor of the computer to calculate and record into the non-volatile memory the indicative property of a fraction of the oil sample as a function of a mid-boiling point of the oil sample determined from the SD data or an average boiling point of the oil sample determined from the SD data, and a density of the oil sample, and
   wherein the function is two-variable polynomial equation, wherein the two variables are the mid-boiling point determined from the SD data or average boiling point determined from the SD data, and the density of the oil sample, and
   wherein the indicative property is used to determine one or more of engine/fuel performance, usability, flow characteristic, or composition of the gas oil fraction or the naphtha fraction of the oil sample.

3. The method of claim 2 wherein the oil sample is crude oil.

4. The method of claim 2 wherein the oil sample is obtained from an oil well, stabilizer, extractor, or distillation tower.

5. The method of claim 2 wherein the indicative property is a cetane number.

6. The method of claim 2 wherein the indicative property is a pour point.

7. The method of claim 2 wherein the indicative property is a cloud point.

8. The method of claim 2 wherein the indicative property is an aniline point.

9. The method of claim 2 wherein the indicative property is an octane number.

10. The method of claim 2 wherein plural indicative properties are calculated including at least two indicative properties selected from the group consisting of cetane number, pour point, cloud point, aniline point and octane number.

11. The method of claim 2, wherein the SD data is obtained from gas chromatography methods including ASTM D2887, ASTM D5236, ASTM D5399, ASTM D6352-04, ASTM D7213-05e1, ASTM D7398-07, ASTM D7169-05, ASTM D7096-10, ASTM D7500-10, and ASTM D5307-97.

12. The method of claim 2, wherein the SD data is obtained from supercritical fluid chromatography methods.

13. The method of claim 2, wherein the two variables are the mid-boiling point determined from the SD data, and the density of the oil sample.

14. The method of claim 13, wherein the mid-boiling point of the crude oil is calculated at the 50 W % point of the SD data.

15. The method of claim 2, wherein the two variables are the average boiling point determined from the SD data, and the density of the oil sample.

16. The method of claim 15, wherein the average boiling point is calculated by taking the weighted average of boiling points.

17. The method of claim 2, wherein correlative SD data is obtained from distillation methods selected from the group composed of ASTM D86, ASTM D1160, ASTM D2892, or any other methods based upon true boiling point distillation, supercritical fluid chromatography, and equilibrium flash.

18. The method as in claim 17, wherein the true boiling point distillations were conducted in a column with the number of theoretical trays in the range 0-100.

19. The method as in claim 17, wherein the true boiling point distillations were conducted in a column with the number of theoretical trays in the range 10-30.

20. The method as in claim 17, wherein the true boiling point distillations were conducted in a column with the number of theoretical trays in the range 15-20.

21. The system as in claim 1, wherein the two-variable polynomial equation is $$\text{Indicative Property } (IP) = K_{IP} + X1_{IP} * DEN + X2_{IP} * DEN^2 + X3_{IP} * DEN^3 + X4_{IP} * (T_{MBP \text{ or } ABP})$$

$$1000) + X5_{IP}*(T_{MBP \text{ or } ABP}/1000)^2 + X6_{IP}*(T_{MBP \text{ or } ABP}/1000)^3 + X7_{IP}*DEN*(T_{MBP \text{ or } ABP}/1000)$$

where

Indicative Property (IP) is selected from the group consisting of cetane number, pour point, cloud point, aniline point and octane number;

DEN is the density of the oil sample;

$T_{MBP \text{ or } ABP}$ is the mid-boiling point of the oil sample determined from the SD data or the average boiling point of the oil sample determined from the SD data;

and $K_{IP}$, $X1_{IP}$, $X2_{IP}$, $X3_{IP}$, $X4_{IP}$, $X5_{IP}$, $X6_{IP}$ and $X7_{IP}$ are constants determined by linear regression for each of the indicative properties.

22. The method as in claim 2, wherein the two-variable polynomial equation is $$\text{Indicative Property } (IP) = K_{IP} + X1_{IP}*DEN + X2_{IP}*DEN^2 + X3_{IP}*DEN^3 + X4_{IP}*(T_{MBP \text{ or } ABP}/1000) + X5_{IP}*(T_{MBP \text{ or } ABP}/1000)^2 + X6_{IP}*(T_{MBP \text{ or } ABP}/1000)^3 + X7_{IP}*DEN*(T_{MBP \text{ or } ABP}/1000)$$

where

Indicative Property (IP) is selected from the group consisting of cetane number, pour point, cloud point, aniline point and octane number;

DEN is the density of the oil sample;

$T_{MBP \text{ or } ABP}$ is the mid-boiling point of the oil sample determined from the SD data or the average boiling point of the oil sample determined from the SD data;

and $K_{IP}$, $X1_{IP}$, $X2_{IP}$, $X3_{IP}$, $X4_{IP}$, $X5_{IP}$, $X6_{IP}$ and $X7_{IP}$ are constants determined by linear regression for each of the indicative properties.

* * * * *